(12) United States Patent
Braunecker et al.

(10) Patent No.: US 7,707,655 B2
(45) Date of Patent: May 4, 2010

(54) SELF WARMING MASK

(75) Inventors: Laura Folkenberg Braunecker, Cumming, GA (US); Kimberly L. Ellefson, Oshkosh, WI (US); Nefetari Bordain Murph, Decatur, GA (US); James Dell Milner, Appleton, WI (US); Curtis N. Sayre, Atlanta, GA (US); Jeffrey Eldon Fish, Dacula, GA (US); Kristi J. Bryant, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 676 days.

(21) Appl. No.: 11/640,481

(22) Filed: Dec. 15, 2006

(65) Prior Publication Data

US 2008/0141437 A1    Jun. 19, 2008

(51) Int. Cl.
*A61F 7/00* (2006.01)
(52) U.S. Cl. .......................... 2/206; 607/109
(58) Field of Classification Search .......... 2/206, 2/15, 9, 171.2, 174; 607/109, 114, 112, 108; 128/206.16, 202.18
See application file for complete search history.

(56) References Cited

U.S. PATENT DOCUMENTS

| | | | |
|---|---|---|---|
| 2,237,971 A | 4/1941 | Padelford | |
| 2,626,343 A | 1/1953 | Fogel et al. | |
| 3,140,390 A | 7/1964 | Smith et al. | |
| 3,173,419 A | 3/1965 | Dubilier et al. | |
| 3,494,821 A | 2/1970 | Evans | |
| 3,855,046 A | 12/1974 | Hansen et al. | |
| 4,100,324 A | 7/1978 | Anderson et al. | |
| 4,144,370 A | 3/1979 | Boulton | |
| 4,243,041 A * | 1/1981 | Paul | 607/109 |
| D258,532 S | 3/1981 | Wagner | |
| 4,323,534 A | 4/1982 | DesMarais | |

(Continued)

FOREIGN PATENT DOCUMENTS

EP    1 090 614 A    4/2001

(Continued)

OTHER PUBLICATIONS

PCT Search Report and Written Opinion for International Application No. PCT/IB2007/054681 dated Mar. 11, 2008.

(Continued)

*Primary Examiner*—Amy B Vanatta
(74) *Attorney, Agent, or Firm*—Dority & Manning, P.A.

(57) ABSTRACT

A self warming mask is disclosed. The self warming mask includes a facing layer configured to cover at least a portion of a person's face. Attached to the facing layer is at least one thermal delivery pad. The thermal delivery pad contains an exothermic composition. Once the mask is removed from a sealed package, air contacts the thermal delivery pad causing the mask to elevate in temperature. The thermal delivery pad can be constructed so that the rise of temperature and the length of time the mask remains heated is carefully controlled. The mask product can be used in combination with a fragrance or vapor delivery device for also releasing a fragrance, a vapor, or both as the mask is heated. In one embodiment, the fragrance or vapor delivery device can be attached and removed to the mask as a user desires.

35 Claims, 3 Drawing Sheets

U.S. PATENT DOCUMENTS

| | | | |
|---|---|---|---|
| 4,517,972 A * | 5/1985 | Finch, Jr. ................... 602/2 |
| 4,559,047 A | 12/1985 | Kapralis et al. |
| 4,614,189 A | 9/1986 | MacKenzie |
| 4,659,609 A | 4/1987 | Lamers et al. |
| 4,663,220 A | 5/1987 | Wisneski et al. |
| 4,795,668 A | 1/1989 | Krueger et al. |
| 4,833,003 A | 5/1989 | Win et al. |
| 4,834,738 A | 5/1989 | Kielpikowski et al. |
| D320,457 S | 10/1991 | Dickinson |
| 5,057,368 A | 10/1991 | Largman et al. |
| 5,069,970 A | 12/1991 | Largman et al. |
| 5,093,422 A | 3/1992 | Himes |
| 5,108,820 A | 4/1992 | Kaneko et al. |
| 5,162,074 A | 11/1992 | Hills |
| D332,310 S | 1/1993 | Ahlen |
| 5,272,236 A | 12/1993 | Lai et al. |
| 5,277,976 A | 1/1994 | Hogle et al. |
| 5,278,272 A | 1/1994 | Lai et al. |
| 5,284,703 A | 2/1994 | Everhart et al. |
| 5,304,599 A | 4/1994 | Himes |
| 5,332,613 A | 7/1994 | Taylor et al. |
| 5,336,552 A | 8/1994 | Strack et al. |
| 5,350,624 A | 9/1994 | Georger et al. |
| 5,382,400 A | 1/1995 | Pike et al. |
| 5,466,410 A | 11/1995 | Hills |
| 5,539,056 A | 7/1996 | Yang et al. |
| 5,540,911 A | 7/1996 | Hartman et al. |
| 5,596,052 A | 1/1997 | Resconi et al. |
| 5,620,779 A | 4/1997 | Levy et al. |
| 5,643,336 A | 7/1997 | Lopez-Claros |
| 5,693,385 A | 12/1997 | Parks |
| 5,700,238 A | 12/1997 | Hyson |
| D390,708 S | 2/1998 | Brown |
| D392,742 S | 3/1998 | Clark, Sr. |
| 5,727,544 A | 3/1998 | Miura |
| 5,760,085 A | 6/1998 | Beck et al. |
| D396,294 S | 7/1998 | Lahr |
| 5,834,114 A | 11/1998 | Economy et al. |
| 5,843,057 A | 12/1998 | McCormack |
| 5,855,999 A | 1/1999 | McCormack |
| 5,932,497 A | 8/1999 | Morman et al. |
| 5,935,883 A | 8/1999 | Pike |
| 5,962,112 A | 10/1999 | Haynes et al. |
| 5,989,004 A | 11/1999 | Cook |
| 5,997,981 A | 12/1999 | McCormack et al. |
| 6,002,064 A | 12/1999 | Kobylivker et al. |
| 6,015,764 A | 1/2000 | McCormack et al. |
| 6,037,281 A | 3/2000 | Mathis et al. |
| D428,267 S | 7/2000 | Romano, III et al. |
| 6,090,403 A | 7/2000 | Block et al. |
| 6,092,521 A | 7/2000 | Miura |
| 6,093,665 A | 7/2000 | Sayovitz et al. |
| 6,103,061 A | 8/2000 | Anderson et al. |
| 6,111,163 A | 8/2000 | McCormack et al. |
| 6,123,996 A | 9/2000 | Larsson et al. |
| 6,155,995 A | 12/2000 | Lin |
| 6,193,740 B1 | 2/2001 | Rodriguez |
| 6,197,404 B1 | 3/2001 | Varona |
| 6,200,669 B1 | 3/2001 | Marmon et al. |
| 6,241,711 B1 | 6/2001 | Weissberg et al. |
| 6,248,880 B1 | 6/2001 | Karlson |
| 6,315,864 B2 | 11/2001 | Anderson et al. |
| 6,409,746 B1 | 6/2002 | Igaki et al. |
| 6,461,457 B1 | 10/2002 | Taylor et al. |
| 6,465,709 B1 | 10/2002 | Sun et al. |
| 6,517,906 B1 | 2/2003 | Economy et al. |
| 6,537,308 B2 | 3/2003 | Burkhart |
| 6,544,284 B1 | 4/2003 | Ujihara et al. |
| 6,544,386 B1 | 4/2003 | Krzysik et al. |
| 6,573,212 B2 | 6/2003 | McCrae et al. |
| 6,576,004 B2 * | 6/2003 | Johnston ................... 607/114 |
| 6,615,838 B1 | 9/2003 | Tsai |
| 6,623,517 B1 | 9/2003 | DeLuisa et al. |
| 6,639,004 B2 | 10/2003 | Falat et al. |
| 6,639,066 B2 | 10/2003 | Boström et al. |
| 6,758,215 B2 | 7/2004 | Begum |
| 6,794,024 B1 | 9/2004 | Walton et al. |
| 6,823,860 B2 | 11/2004 | Igaki et al. |
| 6,823,868 B1 | 11/2004 | Begum |
| 6,824,557 B2 | 11/2004 | Tone et al. |
| 6,827,080 B2 | 12/2004 | Fish et al. |
| 6,890,553 B1 | 5/2005 | Sun et al. |
| 6,893,453 B2 | 5/2005 | Agarwal et al. |
| 6,974,470 B2 | 12/2005 | Tsunakawa et al. |
| 7,021,064 B2 | 4/2006 | Wohland et al. |
| 7,036,503 B2 * | 5/2006 | Miyazawa et al. ..... 128/201.13 |
| 7,047,970 B2 | 5/2006 | Umeda et al. |
| 7,074,234 B2 | 7/2006 | Tone et al. |
| 7,395,554 B2 * | 7/2008 | Kitayama ................... 2/15 |
| 2001/0042546 A1 * | 11/2001 | Umeda et al. .......... 128/206.21 |
| 2002/0141961 A1 | 10/2002 | Falat et al. |
| 2002/0151600 A1 | 10/2002 | Nagashima et al. |
| 2003/0047186 A1 | 3/2003 | Dyer |
| 2003/0056281 A1 | 3/2003 | Hasegawa |
| 2003/0167556 A1 * | 9/2003 | Kelley |
| 2004/0015220 A1 | 1/2004 | Um et al. |
| 2004/0035410 A1 | 2/2004 | Igaki et al. |
| 2004/0138729 A1 * | 7/2004 | Ladmer ................... 607/109 |
| 2004/0166248 A1 | 8/2004 | Hu et al. |
| 2005/0169973 A1 | 8/2005 | Kim |
| 2005/0187597 A1 | 8/2005 | Vanderschuit |
| 2005/0192653 A1 | 9/2005 | Tsunakawa et al. |
| 2006/0141882 A1 | 6/2006 | Quincy et al. |
| 2006/0154006 A1 | 7/2006 | Usui et al. |
| 2006/0191272 A1 | 8/2006 | Wohland et al. |
| 2007/0141934 A1 | 6/2007 | Sayre et al. |
| 2007/0142882 A1 | 6/2007 | Quincy et al. |
| 2007/0144697 A1 | 6/2007 | Dyer et al. |

FOREIGN PATENT DOCUMENTS

| | | |
|---|---|---|
| EP | 0 776679 B1 | 4/2002 |
| EP | 1 393699 A | 3/2004 |
| EP | 1 623689 A1 | 2/2006 |
| EP | 1 632202 A | 3/2006 |
| JP | 2002 369835 A | 12/2002 |
| JP | 2004 148064 A | 5/2004 |
| WO | WO 2004 110541 | 12/2004 |

OTHER PUBLICATIONS

S. Brunauer et al.—*Adsorption of Gases in Muftimolecular Layers*—Journal of the American Chemical Society 1938 vol. 60, pp. 309-319.

* cited by examiner

SELF WARMING MASK

BACKGROUND

Almost everyone, at one time or another, is inflicted with the common cold. For decades, researchers have been attempting to find a cure that prevents people from getting a cold or that shortens the life of a cold once various symptoms are present.

Currently, there are various medications and treatments available for treating the symptoms of colds, such as congestion, sinus pressure and pain, headaches, and other upper respiratory conditions. For instance, numerous over the counter medications are available that are intended to provide some relief. These medications, however, rarely provide immediate relief since they typically require time for the body to metabolize the drugs and then usually only provide relief for a limited period of time.

In addition to over the counter medications that are taken orally, various inhalation therapies are available. For instance, pressurized aerosol products are available that are inhaled. Nebulizers and hot water vaporizers are also used. In addition, various decongestants, such as camphor, are sometimes applied to the throat and chest to help relieve cough and cold symptoms.

Vaporizers, inhalers, and nebulizers as described above, however, do not allow the direct application of heat at the source of symptoms, such as over the sinus cavities. Thus, in some applications, heat may separately be applied to the face and chest of the user during use of the above treatments. Heat is also applied to the face and chest of the user. Most products that are intended to deliver heat, however, are usually somewhat complicated and require an external power source in order to heat the product. For instance, several heating products exist that require microwaving, boiling, or some other external energy supply.

In view of the above, a need currently exists for a product that provides quick relief for a person suffering from congestion, sinus pressure and pain that is self warming and does not require an external heating or power source to provide heat. A need also exists for a self warming product that is also capable of providing aromatherapy to the user if desired. Such a product may be used to not only treat a person suffering from a sinus congestion, a headache, or other related upper respiratory condition but may also be used in any other application wherein heat and/or a fragrance is desired such as in a spa application or the like.

SUMMARY

In general, the present disclosure is directed to a self warming device, such as a self warming mask. The mask, for instance, can be placed on the face of a user and, once activated, can release heat. In particular, the mask is configured to release heat in carefully controlled amounts. The mask can be used in numerous applications. For instance, in one embodiment, the mask can be used to treat a person suffering from congestion, sinus pain and pressure, headaches, or other related upper respiratory conditions. In an alternative embodiment, the mask can be used for pain relief. In still another embodiment, the mask can be used in therapeutic applications, such as in a spa setting.

In addition to delivering heat, the mask can also be configured to release a fragrance or a vapor. The fragrance can be, for instance, any suitable essential oil including oil extracts or other fragrance emitting components. Suitable vapors that may be released by the mask include aromatic decongestants.

In one embodiment, for instance, the present disclosure is directed to a warming mask product that includes a sealed package containing a mask having a shape configured to cover at least a portion of a person's face. The mask, for instance, may have a shape configured to cover the forehead and cheeks of a user. Alternatively, the mask may be relatively small in size and configured only to cover one particular portion of a person's face. The mask includes at least one thermal delivery pad that comprises an exothermic composition contained in a sealed compartment. The compartment comprises a gas permeable polymer film.

The thermal delivery pad includes a first side configured to face a user and a second and opposite side. The gas permeable polymer film can be present on at least the second side of the thermal delivery pad. The mask further includes a facing layer located on the first side of the sealed compartment. The facing layer can be attached to the thermal delivery pad by any suitable means, such as by using an adhesive or through thermal bonding or ultrasonic bonding. The facing layer defines an exterior surface configured to contact the user's face. The facing layer can comprise a single layer of material or can comprise a laminate. In one embodiment, the facing layer contains a nonwoven material.

In accordance with the present disclosure, the exothermic composition is configured to generate heat when exposed to oxygen. Thus, in one embodiment, once the mask is removed from the sealed package, air can pass through the gas permeable polymer film of the thermal delivery pad and react with the exothermic composition thereby releasing heat. The gas permeable polymer film can be constructed so as to carefully control not only the maximum temperature rise of the thermal delivery pad, but also the length of time the pad remains heated. For instance, in one embodiment, the thermal delivery pad can heat to a temperature of at least about 38° C., such as from about 40° C. to about 45° C. In one embodiment, for instance, the thermal delivery pad is heated to a temperature such that when applied to a user's skin, the skin temperature exceeds at least about 38° C. but does not exceed about 43° C. For instance, in one particular embodiment, the mask is configured to raise the temperature of the skin of a user to from about 40° C. to about 42.5° C. The thermal delivery pad can remain at the elevated temperature for at least about 15 minutes, such as from about 30 minutes to about 4 hours or even longer.

In one embodiment, the mask can have user controls for adjusting the amount of heat that the mask gives off. For instance, various gas impermeable strips can be attached to the gas permeable polymer film that are intended to be removed by the user. In one embodiment, multiple strips may be present on the gas permeable polymer film. A user can adjust the amount of heat emitted by the mask by selectively removing one or more strips. For instance, removing all of the strips would create the highest temperature at perhaps the shortest duration. Removing only a selected portion of the strips, on the other hand, may cause the mask to heat to a lower temperature but for a longer duration.

The exothermic composition contained within the thermal delivery pad can vary depending upon the particular application. In one embodiment, for instance, the exothermic composition comprises an oxidizable metal, such as iron, zinc, aluminum, magnesium, alloys thereof, or mixtures thereof. In addition, the exothermic composition can also contain carbon, water, and any other suitable ingredients.

Although optional, in one embodiment, the mask can further include an outer cover layer. For example, the thermal delivery pad can be positioned between the facing layer and an outer cover layer when present. The outer cover layer can be bonded to the facing layer in a manner that secures the thermal delivery pad between the two layers. The outer cover layer can be made from any suitable gas permeable material that will allow air to reach the gas permeable polymer film present on the thermal delivery pad. For instance, the outer cover layer may comprise a nonwoven web.

As described above, the mask comes in any suitable shape depending upon the portion of a person's face that is intended to be covered. In one embodiment, for instance, the mask can include two eye openings. The mask can have a forehead portion positioned over the eye openings and cheek portions that extend down from the eye openings and are configured to border the nose of a wearer. At least one thermal delivery pad can be present in the mask so as to be present along the forehead portion and along the cheek portions. For instance, in one embodiment, the mask can include a first thermal delivery pad that partially encircles the first eye opening extending from the forehead portion to a first cheek portion and a second thermal delivery pad that partially encircles the second eye opening also extending from the forehead portion to the second cheek portion. When the mask is used to treat the common cold or a sinus infection, the mask may also include an open portion below the nose that allows access to the nostrils.

In addition to having a variety of shapes, the mask of the present disclosure can come with any suitable color or design. For instance, in one embodiment, a color, design, pattern or other indicia may be present on an exterior surface of the mask to indicate that the user is not feeling well or sick. When the mask is to be used in a spa setting and/or to be used for therapeutic purposes only, the mask may have a color, design, pattern or other indicia that invokes a soothing feeling. In addition, any indicia of a manufacturer or retailer can also be displayed on the mask. For instance, in one embodiment, the mask can be associated with a logo and/or a brand name of a manufacturer of, for instance, a decongestant product or pain relief product.

In order to adhere or attach the mask to a user's face, the mask can include a strap that is configured to go around a person's head. The strap can be made from any suitable material, such as an elastic laminate. Alternatively, the mask can include a body adhesive for adhering the mask to a user's face. The body adhesive may comprise a pressure sensitive adhesive or a hydrogel.

In addition to delivering heat, the mask can also be configured to deliver a vapor or fragrance. In this regard, a vapor or fragrance delivery device can be packaged with the mask. The vapor or fragrance delivery device can be integrated into the mask or can be a separate device that is attached and/or removed to the mask after the mask is removed from the sealed package. In order to attach the vapor or fragrance delivery device to the mask, the vapor or fragrance delivery device can include any suitable attachment device such as an adhesive or a hook material that forms a hook and loop attachment with the mask.

The vapor or fragrance delivery device can comprise any suitable vehicle for carrying a vapor or fragrance composition. For instance, the vapor or fragrance delivery device can comprise a substrate that contains a vapor or fragrance composition. The vapor or fragrance delivery device can be positioned on the mask so as to be adjacent to the nose of a wearer. As the mask is heated, the heat that is generated by the thermal delivery pad facilitates the emission of vapors and/or fragrance from the vapor or fragrance delivery device.

The vapor or fragrance composition can contain numerous components capable of delivering a vapor or aroma. For instance, the vapor or fragrance composition can contain one or more essential oils. Alternatively, especially when treating the common cold, the vapor or fragrance composition can contain an aromatic decongestant.

Other features and aspects of the present disclosure are discussed in great detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Repeat use of reference characters in the present specification and drawings is intended to represent same or analogous features or elements of the present disclosure.

DETAILED DESCRIPTION

It is to be understood by one of ordinary skill in the art that the present discussion is a description of exemplary embodiments only, and is not intended as limiting the broader aspects of the present disclosure.

The present disclosure is generally directed to a self-heating disposable mask that is capable of raising the skin temperature to a therapeutic temperature. If desired, the mask can also release a fragrance and/or vapor. Most commercially available heating devices for upper respiratory conditions require some sort of external power source such as microwaving or boiling in hot water. The mask of the present disclosure, on the other hand, includes a self-heating technology and can be used in conjunction with a fragrance and/or vapor delivery system.

As will be described in greater detail below, the warming mask of the present disclosure is comprised of disposable textile materials, such as nonwoven materials in conjunction with at least one thermal delivery pad. Of particular advantage, the thermal delivery pad is configured to maintain a controlled and tight temperature range when heated. The thermal delivery pad can also maintain an elevated temperature for an extended period of time providing long lasting therapeutic heat. When the thermal delivery device is combined with a vapor or fragrance delivery device, the heat emitted by the thermal delivery device can facilitate the generation of vapors and/or fragrances that can provide therapeutic value to the user.

The warming mask of the present disclosure can be used in numerous applications. For instance, in one embodiment, the mask can be used to treat various ailments, such as the common cold. The self-warming mask can also be used to provide quick relief to a person suffering from a sinus congestion, a headache, or any other related upper respiratory condition. The self-warming mask can also be used to provide pain relief to the user. For instance, the warming mask may be used to provide pain relief to a user who has undergone some type of face surgery or has suffered any type of trauma to the face.

In still another embodiment, the self-warming mask can be used purely for a therapeutic or calming effect. The mask may help a person relax at home or in a spa setting. In fact, when used in conjunction with various fragrances, the mask can provide aroma therapy as well as heat therapy.

Figure 1:
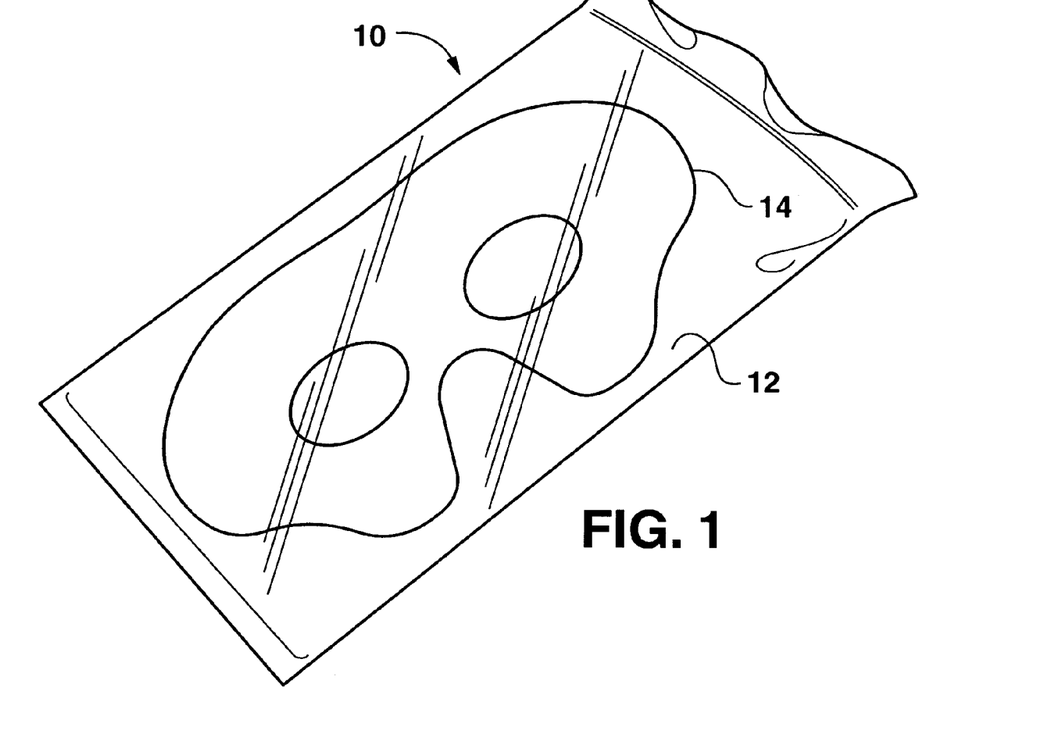
FIG. 1 is a perspective view of one embodiment of a warming mask product in accordance with the present disclosure.

Referring to FIG. 1, one embodiment of a self-warming mask product generally 10 is shown. The mask product 10, in this embodiment includes a sealed package 12 containing a mask 14. The sealed package 12 can be made from any suitable material that is substantially gas impermeable. The purpose of the sealed package 12 is to prevent exposure of the mask 14 to ambient air which will cause the mask to activate and heat up. The sealed package 12, for instance, can be made from polymer films and from polymer film laminates. In one embodiment, for instance, the sealed package 12 is made from a film laminate containing a metalized or foil layer. If desired, the sealed package 12 can include a weakened portion that allows one to easily open the package through a tearing motion.

Figure 2:
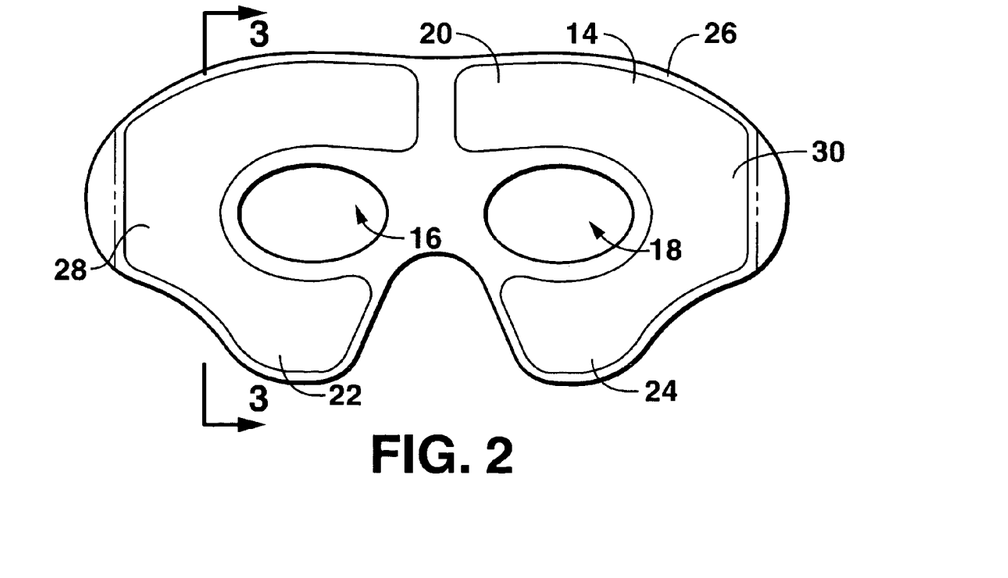
FIG. 2 is a plan view of a mask contained in the warming mask product illustrated in FIG. 1.

Referring to FIG. 2, a plan view of the mask 14 is shown after being removed from the sealed package. It should be understood that the mask 14 can be configured to cover any suitable portion of a person's face. The shape of the mask, for instance, may depend upon the intended use of the mask. For instance, a mask designed for therapeutic spa-like benefits may have a different shape than a mask used to treat sinus infections and the like. In fact, the mask can be designed to cover the entire face, neck and chest of a user.

In an alternative embodiment, the mask can be designed to cover a relatively small portion of a person's face. For instance, the mask may comprise an adhesive strip that is configured to be placed on a particular location on the face. For instance, when the mask is used to treat sinus infections and/or colds, the mask may be in the form of adhesive strips that are designed to cover the sinus areas such as the forehead and under the eyes, For instance, in one particular embodiment, several masks may be packaged together allowing a user to selectively put each mask where desired. In this embodiment, each mask may have the same shape or may have a different shape. For instance, a strip-like mask designed to cover the forehead may have a rectangular shape. A strip-like mask designed to be placed under the eyes of a person or on the cheeks, however, may have a more circular shape.

In the embodiment illustrated in FIG. 2, however, the mask is designed to cover a person's forehead and to surround the eyes and nose of a user. In this regard, the mask 14 includes a first eye opening 16 spaced from a second eye opening 18. The mask 14 further includes a forehead portion 20 located above the eye openings 16 and 18. In addition, the mask 14 includes a pair of lobes that extend downwardly. Specifically, the mask includes a first cheek portion 22 that extends downwardly from the first eye opening 16 and a second cheek portion 24 that extends downwardly from the second eye opening 18. The cheek portions 22 and 24 are designed to surround the nose of a user.

When the mask 14 is designed to treat a person suffering from congestion, sinus pressure and pain, it is generally desirable that the mask does not surround the nose of a user so that a user can continue to blow his or her nose even while wearing the mask. For instance, as shown in FIG. 2, the mask 14 includes an access area for the nostrils. In other applications, however, if desired, the mask may also include a nose portion that also covers the nose of a user. The nose portion, for instance, may comprise an elastic material, a gathered material that has sufficient slack to go over the nose of a user, or may project outwardly from the mask so that the nose can fit comfortably below the mask. The mask may include a nose portion, for instance, when it is desirable to apply heat directly to the nose of a user, such as during a spa application or perhaps to provide pain relief when the nose has been injured.

Figure 3:
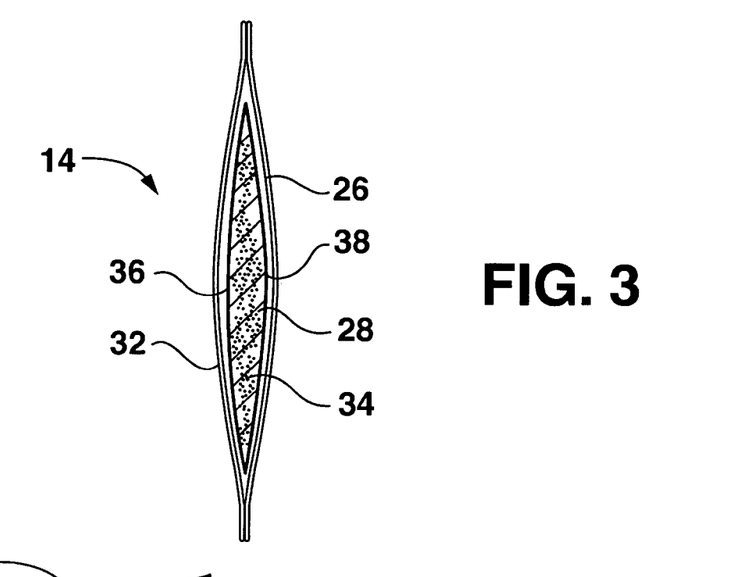
FIG. 3 is a side view of the mask illustrated in FIG. 2.

The mask 14 as shown in FIG. 2 includes a facing layer 26 that supports at least one thermal delivery pad. For instance, as shown in FIG. 2, the mask may include a first thermal delivery pad 28 and a second thermal delivery pad 30. Optionally, the mask can include an outer cover 32 as shown in FIG. 3. Although the embodiment in FIG. 2 shows first and second thermal delivery pads 28 and 30, it should be understood that more or less delivery pads may be present. For instance, in one embodiment, the mask may include a single thermal delivery pad that is generally in the shape of the entire mask.

In accordance with the present disclosure, the appearance of the mask 14 can vary depending upon the particular application. For instance, the mask 14 may display a particular color or display a particular pattern. In addition, the mask may be embossed with various patterns and designs. The mask can also be associated with various indicia of a manufacturer or retailer. For instance, any suitable logo and/or brand name may be displayed on the mask. When the mask is used to treat a sinus infection and/or a cold, for instance, a logo or brand name that is typically used in conjunction with cold products, including tissue products, may be displayed on the mask.

In one embodiment, the mask can include some type of indicia that indicates that the user of the mask is not feeling well or sick. For instance, the indicia may be a particular color, pattern, caricature, design, and the like applied to the mask.

The mask may also include various appealing aesthetic properties that may allow a user to feel more comfortable wearing the mask. When the mask is to be used for therapeutic purposes, the mask may display a color, pattern or design that is intended to invoke a soothing feeling or calming effect in the user.

Referring to FIG. 3, the construction of the thermal delivery pad 28 is shown in more detail. As illustrated, the thermal delivery pad 28 includes an exothermic composition 34 sandwiched and sealed in between a first polymer film 36 and a second polymer film 38. In one embodiment, for instance, the exothermic composition may comprise a heat generating composition as described in U.S. Patent Application Publication No. US 2006/0154006 entitled "Exothermic Composition and Exothermic Element" and owned by the Mycoal Products Corporation and which is incorporated herein by reference.

The exothermic composition may be formed from a variety of different components, including oxidizable metals, carbon components, binders, electrolytic salts, and so forth. Examples of such metals include, but are not limited to, iron, zinc, aluminum, magnesium, and so forth. Although not required, the metal may be initially provided in powder form to facilitate handling and to reduce costs. Various methods for removing impurities from a crude metal (e.g. iron) to form a powder include, for example, wet processing techniques, such as solvent extraction, ion exchange, and electrolytic refining for separation of metallic elements; hydrogen gas ($H_2$) processing for removal of gaseous elements, such as oxygen and nitrogen; floating zone melting refining method.

Using such techniques, the metal purity may be at least about 95%, in some embodiments at least about 97%, and in some embodiments, at least about 99%. The particle size of the metal powder may also be less than about 500 micrometers, in some embodiments less than about 100 micrometers, and in some embodiments, less than about 50 micrometers. The use of such small particles may enhance the contact surface of the metal with air, thereby improving the likelihood and efficiency of the desired exothermal reaction. The concentration of the metal powder employed may generally vary depending on the nature of the metal powder, and the desired extent of the exothermal/oxidation reaction. In most embodiments, the metal powder is present in the exothermic composition in an amount from about 40 wt. % to about 95 wt. %, in some embodiments from about 50 wt. % to about 90 wt. %, and in some embodiments, from about 60 wt. % to about 80 wt. %.

In addition to an oxidizable metal, a carbon component may also be utilized in the exothermic composition of the present invention. Without intending to be limited in theory, it is believed that such a carbon component promotes the oxidation reaction of the metal and acts as a catalyst for generating heat. The carbon component may be activated carbon, carbon black, graphite, and so forth. When utilized, activated carbon may be formed from sawdust, wood, charcoal, peat, lignite, bituminous coal, coconut shells, etc. Some suitable forms of activated carbon and techniques for formation thereof are described in U.S. Pat. No. 5,693,385 to Parks; U.S. Pat. No.5,834,114 to Economy, et al.; U.S. Pat. No. 6,517,906 to Economy, et al.; U.S. Pat. No. 6,573,212 to McCrae, et al., as well as U.S. Patent Application Publication No. 2002/0141961 to Falat, et al. and U.S. Patent Application Publication No. 2004/0166248 to Hu, et al., all of which are incorporated herein in their entirety by reference thereto for all purposes.

The exothermic composition may also employ a binder for enhancing the durability of the exothermic composition when applied to a thermal composite. As described in more detail below, the binder may also serve as an adhesive for bonding one thermal composite to another thermal composite. Generally speaking, any of a variety of binders may be used in the exothermic composition of the present invention. Suitable binders may include, for instance, those that become insoluble in water upon crosslinking. Crosslinking may be achieved in a variety of ways, including by reaction of the binder with a polyfunctional crosslinking agent. Examples of such crosslinking agents include, but are not limited to, dimethylol urea melamine-formaldehyde, urea-formaldehyde, polyamide epichlorohydrin, etc.

In some embodiments, a polymer latex may be employed as the binder. The polymer suitable for use in the latexes typically has a glass transition temperature of about 30° C. or less so that the flexibility of the resulting thermal composite is not substantially restricted. Moreover, the polymer also typically has a glass transition temperature of about –25° C. or more to minimize the tackiness of the polymer latex. For instance, in some embodiments, the polymer has a glass transition temperature from about –15° C. to about 15° C., and in some embodiments, from about –10° C. to about 0° C. For instance, some suitable polymer latexes that may be utilized in the present invention may be based on polymers such as, but are not limited to, styrene-butadiene copolymers, polyvinyl acetate homopolymers, vinyl-acetate ethylene copolymers, vinyl-acetate acrylic copolymers, ethylene-vinyl chloride copolymers, ethylene-vinyl chloride-vinyl acetate terpolymers, acrylic polyvinyl chloride polymers, acrylic polymers, nitrile polymers, and any other suitable anionic polymer latex polymers known in the art. The charge of the polymer latexes described above may be readily varied, as is well known in the art, by utilizing a stabilizing agent having the desired charge during preparation of the polymer latex. Specific carbon/polymer latex systems are described in more detail in U.S. Pat. Nos. 6,573,212; 6,639,004; 5,693,385; and U.S. Pat. No 5,540,916Activated carbon/polymer latex systems that may be used in the present invention include Nuchar® PMA, DPX-8433-68A, and DPX-8433-68B, all of which are available from MeadWestvaco Corp of Stamford, Conn.

If desired, the polymer latex may be crosslinked using any known technique in the art, such as by heating, ionization, etc. Preferably, the polymer latex is self-crosslinking in that external crosslinking agents (e.g., N-methylol acrylamide) are not required to induce crosslinking. Specifically, crosslinking agents may lead to the formation of bonds between the polymer latex and the thermal composite to which it is applied. Such bonding may sometimes interfere with the effectiveness of the thermal composite in generating heat. Thus, the polymer latex may be substantially free of crosslinking agents. Particularly suitable self-crosslinking polymer latexes are ethylene-vinyl acetate copolymers available from Celanese Corp. of Dallas, Tex. under the designation DUR-O-SET® Elite (e.g., PE-25220A, PE-LV 25-432A). Alternatively, an inhibitor may simply be employed that reduces the extent of crosslinking, such as free radical scavengers, methyl hydroquinone, t-butylcatechol, pH control agents (e.g., potassium hydroxide), etc.

Although polymer latexes may be effectively used as binders in the present invention, such compounds sometimes result in a reduction in drapability and an increase in residual odor. Thus, the present inventors have discovered that water-soluble organic polymers may also be employed as binders, either alone or in conjunction with the polymer latexes, to alleviate such concerns. For example, one class of water-soluble organic polymers found to be suitable in the present invention is polysaccharides and derivatives thereof (e.g., cellulosic ethers). Polysaccharides are polymers containing repeated carbohydrate units, which may be cationic, anionic, nonionic, and/or amphoteric. In one particular embodiment, for instance, the polysaccharide is a nonionic, cationic, anionic, and/or amphoteric cellulosic ether. Nonionic cellulose ethers, for instance, may be produced in any manner known to those skilled in the art, such as by reacting alkali cellulose with ethylene oxide and/or propylene oxide, followed by reaction with methyl chloride, ethyl chloride and/or propyl chloride. Nonionic cellulosic ethers and methods for producing such ethers are described, for instance, in U.S. Pat. Nos. 6,123,996 to Larsson, et al.; U.S. Pat. Nos. 6,248,880 to Karlson; and U.S. Pat. Nos. 6,639,066 to Bostrom, et al., which are incorporated herein in their entirety by reference thereto for all purposes. Some suitable examples of nonionic cellulosic ethers include, but are not limited to, water-soluble alkyl cellulose ethers, such as methyl cellulose and ethyl cellulose; hydroxyalkyl cellulose ethers, such as hydroxyethyl cellulose, hydroxypropyl cellulose, hydroxypropyl hydroxybutyl cellulose, hydroxyethyl hydroxypropyl cellulose, hydroxyethyl hydroxybutyl cellulose and hydroxyethyl hydroxypropyl hydroxybutyl cellulose; alkyl hydroxyalkyl cellulose ethers, such as methyl hydroxyethyl cellulose, methyl hydroxypropyl cellulose, ethyl hydroxyethyl cellulose, ethyl hydroxypropyl cellulose, methyl ethyl hydroxyethyl cellulose and methyl ethyl hydroxypropyl cellulose; and so forth. Preferred nonionic cellulosic ethers for use in the coating composition of the present invention are ethyl hydroxyethyl cellulose, methylethyl hydroxyethyl cellulose, methylethyl hydroxyethyl hydroxypropyl cellulose and methyl hydroxypropyl cellulose. In such embodiments, the hydroxyethyl groups typically constitute at least 30% of the total number of hydroxyalkyl groups, and the number of ethyl substituents typically constitutes at least 10% of the total number of alkyl substituents.

Particularly suitable cellulosic ethers may include, for instance, those available from Akzo Nobel of Stamford, Conn. under the name "BERMOCOLL." Still other suitable cellulosic ethers are those available from Shin-Etsu Chemical Co., Ltd. of Tokyo, Japan under the name "METOLOSE", including METOLOSE Type SM (methycellulose), METOLOSE Type SH (hydroxypropylmethyl cellulose), and METOLOSE Type SE (hydroxyethylmethyl cellulose). One particular example of a suitable nonionic cellulosic ether is methylcellulose having a degree of methoxyl substitution (DS) of 1.8. The degree of methoxyl substitution represents the average number of hydroxyl groups present on each anhydroglucose unit that have been reacted, which may vary between 0 and 3. One such cellulosic ether is METOLOSE SM-100, which is a methylcellulose commercially available from Shin-Etsu Chemical Co., Ltd. Other suitable cellulosic ethers are also available from Hercules, Inc. of Wilmington, Del. under the name "CULMINAL." Further examples of suitable polysaccharides are described in more detail above.

The concentration of the carbon component and/or binder in the exothermic composition may generally vary based on the desired properties of the thermal composite. For example, the amount of the carbon component is generally tailored to facilitate the oxidation/exothermic reaction without adversely affecting other properties of the thermal composite. Typically, the carbon component is present in the exothermic composition in an amount about 0.01 wt. % to about 20 wt. %, in some embodiments from about 0.1 wt. % to about 15 wt. %, and in some embodiments, from about 1 wt. % to about 12 wt. %. In addition, although relatively high binder concentrations may provide better physical properties for the exothermic composition, they may likewise have an adverse effect on other properties, such as the absorptive capacity of the thermal composite to which it is applied. Conversely, relatively low binder concentrations may reduce the ability of the exothermic composition to remain affixed on the thermal composite. Thus, in most embodiments, the binder is present in the exothermic composition in an amount from about 0.01 wt. % to about 20 wt. %, in some embodiments from about 0.1 wt. % to about 10 wt. %, and in some embodiments, from about 0.5 wt. % to about 8 wt. %.

Still other components may also be employed in the exothermic composition of the present invention. For example, as is well known in the art, an electrolytic salt may be employed to react with and remove any passivating oxide layer(s) that might otherwise prevent the metal from oxidizing. Suitable electrolytic salts may include, but are not limited to, alkali halides or sulfates, such as sodium chloride, potassium chloride, etc.; alkaline halides or sulfates, such as calcium chloride, magnesium chloride, etc., and so forth. When employed, the electrolytic salt is typically present in the exothermic composition in an amount from about 0.01 wt. % to about 10 wt. %, in some embodiments from about 0.1 wt. % to about 8 wt. %, and in some embodiments, from about 1 wt. % to about 6 wt. %.

In addition, particles may also be employed in the exothermic composition that acts as moisture retainers. That is, prior to the oxidation/exothermic reaction, these particles may retain moisture. However, after the reaction has proceeded to a certain extent and the moisture concentration is reduced, the particles may release the moisture to allow the reaction to continue. Besides acting as a moisture retainer, the particles may also provide other benefits to the exothermic composition of the present invention. For example, the particles may alter the black color normally associated with the carbon component and/or metal powder. When utilized, the size of the moisture-retaining particles may be less than about 500 micrometers, in some embodiments less than about 100 micrometers, and in some embodiments, less than about 50 micrometers. Likewise, the particles may be porous. Without intending to be limited by theory, it is believed that porous particles may provide a passage for air and/or water vapors to better contact the metal powder. For example, the particles may have pores/channels with a mean diameter of greater than about 5 angstroms, in some embodiments greater than about 20 angstroms, and in some embodiments, greater than about 50 angstroms. The surface area of such particles may also be greater than about 15 square meters per gram, in some embodiments greater than about 25 square meters per gram, and in some embodiments, greater than about 50 square meters per gram. Surface area may be determined by the physical gas adsorption (B.E.T.) method of Bruanauer, Emmet, and Teller, *Journal of American Chemical Society*, Vol. 60, 1938, p. 309, with nitrogen as the adsorption gas.

In one particular embodiment, porous carbonate particles (e.g., calcium carbonate) are used to retain moisture and also to alter the black color normally associated with activated carbon and/or metal powder. Such a color change may be more aesthetically pleasing to a user, particularly when the coating is employed on thermal composites designed for consumer/personal use. Suitable white calcium carbonate particles are commercially available in both dry and aqueous slurry form from Omya, Inc. of Proctor, Vt. Still other suitable inorganic particles that may retain moisture include, but are not limited to, silicates, such as calcium silicate, alumina silicates (e.g., mica powder, clay, etc.), magnesium silicates (e.g., talc), quartzite, calcium silicate fluorite, vermiculite, etc.; alumina; silica; and so forth. The concentration of the particles may generally vary depending on the nature of the particles, and the desired extent of exothermic reaction and color alteration. For instance, the particles may be present in the exothermic composition in an amount from about 0.01 wt. % to about 30 wt. %, in some embodiments from about 0.1 wt. % to about 20 wt. %, and in some embodiments, from about 1 wt. % to about 15 wt. %.

In addition to the above-mentioned components, other components, such as surfactants, pH adjusters, dyes/pigments/inks, viscosity modifiers, etc., may also be included in the exothermic coating of the present invention. Viscosity modifiers may be used, for example, to adjust the viscosity of the coating formulation based on the desired coating process and/or performance of the coated thermal composite. Suitable viscosity modifiers may include gums, such as xanthan gum. Binders, such as the cellulosic ethers, may also function as suitable viscosity modifiers. When employed, such additional components typically constitute less than about 5 wt. %, in some embodiments less than about 2 wt. %, and in some embodiments, from about 0.001 wt. % to about 1 wt. % of the exothermic coating.

In addition, the exothermic composition may also contain water. Water may be intimately mixed with the composition or present in an adjacent layer. When mixed with the exothermic composition, water can be used as a binder. Specifically, water can cause the components to bond together by surface tension. Water can also be present in the exothermic composition to provide fluidity allowing the composition to be molded and to have some shape-holding properties. Water can be present in the exothermic composition in an amount from about 5% to about 60% by weight, such as from about 20% to about 50% by weight.

The amount of the other components added to the formulation may vary depending on the amount of heat desired, the wet pick-up of the application method utilized, etc. For example, the amount of the oxidizable metal (in powder form) within the coating formulation generally ranges from about 20 wt. % to about 80 wt. %, in some embodiments from about 30 wt. % to about 70 wt. %, and in some embodiments, from about 35 wt. % to about 60 wt. %. In addition, the carbon component may constitute from about 0.1 wt. % to about 20 wt. %, in some embodiments from about 0.1 wt. % to about 15 wt. %, and in some embodiments, from about 0.2 wt. % to about 10 wt. % of the coating formulation. Binders may constitute from about 0.01 wt. % to about 20 wt. %, in some embodiments from about 0.1 wt. % to about 15 wt. %, and in some embodiments, from about 1 wt. % to about 10 wt. % of the coating formulation. Electrolytic salts may constitute from about 0.01 wt. % to about 10 wt. %, in some embodiments from about 0.1 wt. % to about 8 wt. %, and in some embodiments, from about 1 wt. % to about 5 wt. % of the coating formulation. Further, moisture-retaining particles (e.g., calcium carbonate) may constitute from about 2 wt. % to about 30 wt. %, in some embodiments from about 3 wt. % to about 25 wt. %, and in some embodiments, from about 4 wt. % to about 10 wt. % of the coating formulation. Other components, such as surfactants, pH adjusters, viscosity modifiers, etc., may also constitute from about 0.001 wt. % to about 5 wt. %, in some embodiments from about 0.01 wt. % to about 1 wt. %, and in some embodiments from about 0.02 wt. % to about 0.5 wt. % of the coating formulation.

As described above, the exothermic composition 34 is contained in a thermal delivery pad that, in one embodiment, is formed from a first polymer film 36 and a second polymer film 38. As shown in FIG. 3, the second polymer film 38 is positioned to face a user and to deliver heat. In order to activate the exothermic composition 34, air enters the thermal delivery pad through at least one of the polymer films. In this regard, at least a portion of the thermal delivery pad 28 includes a gas permeable portion. For instance, in one embodiment, at least a portion of the polymer film 36 is gas permeable or breathable, while remaining impermeable to liquids.

The breathable film can comprise, for instance, a microporous or monolithic film or can comprise an apertured film. The film may be formed from a polyolefin polymer, such as linear, low-density polyethylene (LLDPE) or polypropylene. Examples of predominately linear polyolefin polymers include, without limitation, polymers produced from the following monomers: ethylene, propylene, 1-butene, 4-methyl-pentene, 1-hexene, 1-octene and higher olefins as well as copolymers and terpolymers of the foregoing. In addition, copolymers of ethylene and other olefins including butene, 4-methyl-pentene, hexene, heptene, octene, decene, etc., are also examples of predominately linear polyolefin polymers.

If desired, the breathable film may also contain an elastomeric polymer, such as elastomeric polyesters, elastomeric polyurethanes, elastomeric polyamides, elastomeric polyolefins, elastomeric copolymers, and so forth. Examples of elastomeric copolymers include block copolymers having the general formula A-B-A' or A-B, wherein A and A' are each a thermoplastic polymer endblock that contains a styrenic moiety (e.g., poly(vinyl arene)) and wherein B is an elastomeric polymer midblock, such as a conjugated diene or a lower alkene polymer (e.g., polystyrene-poly(ethylene-butylene)-polystyrene block copolymers). Also suitable are polymers composed of an A-B-A-B tetrablock copolymer, such as discussed in U.S. Pat. No. 5,332,613 to Taylor, et al., which is incorporated herein in its entirety by reference thereto for all purposes. An example of such a tetrablock copolymer is a styrene-poly(ethylene-propylene)-styrene-poly(ethylene-propylene) ("S-EP-S-EP") block copolymer. Commercially available A-B-A' and A-B-A-B copolymers include several different formulations from Kraton Polymers of Houston, Tex. under the trade designation KRATON®. KRATON® block copolymers are available in several different formulations, a number of which are identified in U.S. Pat. Nos. 4,663,220, 4,323,534, 4,834,738, 5,093,422 and U.S. Pat. No. 5,304,599, which are hereby incorporated in their entirety by reference thereto for all purposes. Other commercially available block copolymers include the S-EP-S or styrene-poly(ethylene-propylene)-styrene elastomeric copolymer available from Kuraray Company, Ltd. of Okayama, Japan, under the trade name SEPTON®.

Examples of elastomeric polyolefins include ultra-low density elastomeric polypropylenes and polyethylenes, such as those produced by "single-site" or "metallocene" catalysis methods. Such elastomeric olefin polymers are commercially available from ExxonMobil Chemical Co. of Houston, Tex. under the trade designations ACHIEVE® (propylene-based), EXACT® (ethylene-based), and EXCEED® (ethylene-based). Elastomeric olefin polymers are also commercially available from DuPont Dow Elastomers, LLC (a joint venture between DuPont and the Dow Chemical Co.) under the trade designation ENGAGE® (ethylene-based) and AFFINITY® (ethylene-based). Examples of such polymers are also described in U.S. Pat. No. 5,278,272 and U.S. Pat. No. 5,272,236 to Lai, et al., which are incorporated herein in their entirety by reference thereto for all purposes. Also useful are certain elastomeric polypropylenes, such as described in U.S. Pat. No. 5,539,056 to Yang, et al. and U.S. Pat. No. 5,596,052 to Resconi, et al., which are incorporated herein in their entirety by reference thereto for all purposes.

If desired, blends of two or more polymers may also be utilized to form the breathable film. For example, the film may be formed from a blend of a high performance elastomer and a lower performance elastomer. A high performance elastomer is generally an elastomer having a low level of hysteresis, such as less than about 75%, and in some embodiments, less than about 60%. Likewise, a low performance elastomer is generally an elastomer having a high level of hysteresis, such as greater than about 75%. The hysteresis value may be determined by first elongating a sample to an ultimate elongation of 50% and then allowing the sample to retract to an amount where the amount of resistance is zero. Particularly suitable high performance elastomers may include styrenic-based block copolymers, such as described above and commercially available from Kraton Polymers of Houston, Tex. under the trade designation KRATON®. Likewise, particularly suitable low performance elastomers include elastomeric polyolefins, such as metallocene-catalyzed polyolefins (e.g., single site metallocene-catalyzed linear low density polyethylene) commercially available from DuPont Dow Elastomers, LLC under the trade designation AFFINITY®. In some embodiments, the high performance elastomer may constitute from about 25 wt. % to about 90 wt. % of the polymer component of the film, and the low performance elastomer may likewise constitute from about 10 wt. % to about 75 wt. % of the polymer component of the film. Further examples of such a high performance/low performance elastomer blend are described in U.S. Pat. No. 6,794,024 to Walton, et al., which is incorporated herein in its entirety by reference thereto for all purposes.

As stated, the breathable film may be microporous. The micropores form what is often referred to as tortuous pathways through the film. Liquid contacting one side of the film does not have a direct passage through the film. Instead, a network of microporous channels in the film prevents liquids from passing, but allows gases and water vapor to pass. Microporous films may be formed from a polymer and a filler (e.g., calcium carbonate). Fillers are particulates or other forms of material that may be added to the film polymer extrusion blend and that will not chemically interfere with the extruded film, but which may be uniformly dispersed throughout the film. Generally, on a dry weight basis, based on the total weight of the film, the film includes from about 30% to about 90% by weight of a polymer. In some embodiments, the film includes from about 30% to about 90% by weight of a filler. Examples of such films are described in U.S. Pat. No. 5,843,057 to McCormack; U.S. Pat. No. 5,855,999 to McCormack; U.S. Pat. No.5,932,497 to Morman, et al.; U.S. Pat. No.5,997,981 to McCormack et al.; U.S. Pat. No. 6,002,064 to Kobylivker, et al.; U.S. Pat. No. 6,015,764 to McCormack, et al.; U.S. Pat. No. 6,037,281 to Mathis, et al.; U.S. Pat. No. 6,111,163 to McCormack, et al.; and U.S. Pat. No.6,461,457 to Taylor, et al., which are incorporated herein in their entirety by reference thereto for all purposes.

The films are generally made breathable by stretching the filled films to create the microporous passageways as the polymer breaks away from the filler (e.g., calcium carbonate) during stretching. For example, the breathable material contains a stretch-thinned film that includes at least two basic components, i.e., a polyolefin polymer and filler. These components are mixed together, heated, and then extruded into a film layer using any one of a variety of film-producing processes known to those of ordinary skill in the film processing art. Such film-making processes include, for example, cast embossed, chill and flat cast, and blown film processes.

Another type of breathable film is a monolithic film that is a nonporous, continuous film, which because of its molecular structure, is capable of forming a liquid-impermeable, vapor-permeable barrier. Among the various polymeric films that fall into this type include films made from a sufficient amount of poly(vinyl alcohol), polyvinyl acetate, ethylene vinyl alcohol, polyurethane, ethylene methyl acrylate, and ethylene methyl acrylic acid to make them breathable. Without intending to be held to a particular mechanism of operation, it is believed that films made from such polymers solubilize water molecules and allow transportation of those molecules from one surface of the film to the other. Accordingly, these films may be sufficiently continuous, i.e., nonporous, to make them substantially liquid-impermeable, but still allow for vapor permeability.

In still another embodiment, the breathable film may comprise a gas impermeable film that has been apertured. The apertures can have any suitable size depending upon the particular application and the components used to form the exothermic composition.

The amount the thermal delivery pad 28 is made from a breathable film and the permeability of the film depend upon the particular application and desired result. The gas permeable portion of the thermal delivery pad 28 essentially becomes the rate determining vehicle of the exothermic composition by controlling the amount of oxygen that contacts the composition. Of particular advantage, the thermal delivery pad can be designed so as to maintain a controlled and tight temperature range based upon the gas permeability of the pad. For instance, in one embodiment, the thermal delivery pad can have a gas permeability that causes the exothermic composition to heat the pad to a temperature of at least 38° C. such as from about 40° C. to about 45° C. In still another embodiment, the thermal delivery pad can be designed to heat to a temperature from about 40° C. to about 43° C. In general, the thermal delivery pad should heat to a temperature sufficient to provide therapeutic heat to the user but without causing any discomfort. For instance, the mask can be designed to increase the skin temperature of the user of from about 40° C. to about 43° C., such as from about 40° C. to about 42.5° C.

The thermal delivery pad made in accordance to the present disclosure is capable of maintaining a tight temperature range as described above for extended periods of time, such as greater than 15 minutes, such as greater than 1 hour, such as even greater than 2 hours. The amount of time that the thermal delivery pad remains heated can depend upon the particular application. For instance, when the mask is used for aroma therapy or for use in spa-like therapeutic applications, the mask may only need to be heated for a period of time of about 15 minutes. When treating a user for sinus congestion, the common cold, or for pain relief, however, the mask can remain heated for a time of from about 1 hour to about 6 hours, such as from about 2 hours to about 5 hours.

Maintaining a tight temperature range also provides various advantages and benefits. For instance, if the temperature were too low during use, the user may not experience the therapeutic effect of the mask and may not perceive the heat being delivered. If the product were to exceed a temperature greater than about 45° C., on the other hand, the user may experience some discomfort. Most prior products are not capable of maintaining such tight temperature requirements.

In one embodiment, the mask can be designed to have user controls for adjusting the amount of heat that the mask emits. For instance, in one embodiment, the breathable film may be covered by a plurality of blocking members. The blocking members may comprise, for instance, adhesive strips that cover the breathable film. In this embodiment, the user can remove a suitable amount of strips for uncovering a desired portion of the breathable film. Removing a greater amount of blocking members or adhesive strips will cause the temperature of the mask to increase. In this manner, a user can personalize their own temperature setting. For instance, in one particular embodiment, three different blocking members may be attached to the mask. Removing a single blocking member may correspond to a low temperature setting. Removing two of the blocking members, on the other hand, may correspond to a medium temperature setting. Removing all of the blocking members, on the other hand, may correspond to a high temperature setting. In addition to adjusting the temperature, the blocking members may also adjust the amount of time that the mask remains heated. For instance, at lower temperature settings, the mask may remain heated for a longer period of time. At higher temperature settings, on the other hand, the heating duration may be lower.

As described above, the mask product of the present disclosure can include a single thermal delivery pad or can include multiple pads positioned over the mask. In the embodiment illustrated in FIG. 2, the mask includes the first thermal delivery pad 28 and the second thermal delivery pad 30. As shown, the first thermal delivery pad partially encircles the eye opening 16. The thermal delivery pad 28 thus extends into the forehead portion 20 and down into the first cheek portion 22. Similarly, the second thermal delivery pad 30 partially encircles the second eye opening 18 and also delivers heat to the forehead portion 20 and to the second cheek portion 24. In this manner, heat is provided to a user around the eyes, over the forehead, and adjacent to the nose.

The thermal delivery pads 28 and 30 are attached to the facing layer 26 as shown in FIG. 3. The facing layer 26 can comprise generally any suitable fibrous layer that may comprise a single layer of material or may comprise a laminate containing multiple layers of material. The facing layer 26 can be constructed from nonwoven webs, woven fabrics, knit fabrics, paper webs, and the like. Nonwoven webs that may be used to construct the facing layer include spunbonded webs (apertured or non-apertured), meltblown webs, carded webs (bonded or unbonded), airlaid webs, coform webs, hydraulically entangled webs, spunlaced webs, and the like. A wide variety of polymers may be used, such as polyolefins, e.g., polyethylene, polypropylene, polybutylene, and so forth; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; and so forth.

In general, the facing layer 26 can be made from any suitable material that can comfortably rest on a person's face. In one embodiment, various different nonwoven layers can be combined together to form a laminate that is used as the facing layer. The layers of the laminate can be bonded together to form a composite structure using any conventional bonding technique. For instance, the layers can be bonded together using through-airbonding, ultrasonic bonding, thermal point bonding, adhesive bonding, and the like.

The facing layer 26 is suitably attached to the thermal delivery pads 28 and 30. The thermal delivery pads can be attached to the facing layer using any of the bonding techniques described above. For instance, the thermal delivery pad can be thermally bonded, ultrasonically bonded or bonded to the facing layer using an adhesive.

Although optional, the mask can further include the outer cover layer 32 as shown in FIG. 3. The outer cover layer can be included on the product to improve the aesthetics and can be also used to better hold the thermal delivery pads in position. For instance, the outer cover layer can be bonded to the facing layer 26 in a manner that forms pockets for the thermal delivery pads.

If present, the outer cover layer 32 can be made from any of the textile materials described above. The outer cover layer 32, however, must have sufficient gas permeability so as to not interfere with the ability of the thermal delivery pad to receive air for gas diffusion. Thus, if present, the outer cover layer can comprise a nonwoven web having a relatively light basis weight and significant porosity.

In order to hold the mask 14 onto the face of a user, the mask can include a strap and/or an adhesive applied to the facing layer 26. A strap 40, for instance, is shown in the embodiment illustrated in FIG. 7. Strap 40 can be made from any suitable material. In one embodiment, for instance, the strap 40 is comprised of an elastic material. For instance, the strap can be made from an elastic film or an elastic laminate. In one embodiment, for instance, the strap can be made from a stretch bonded laminate or from a neck bonded laminate. Such materials may provide comfort to the user.

Instead of a strap or in addition to the use of a strap, the mask can also include an adhesive for adhering the mask to a person's face. In general, any suitable body adhesive can be used. For instance, the adhesive can comprise a pressure sensitive adhesive. Alternatively, a gel-like adhesive may be used, such as a hydrogel. In one embodiment, the adhesive may provide better heat delivery to the face of the user after the exothermic composition has been activated.

In addition to providing heat to the user, the mask product of the present disclosure can also include a vapor or fragrance delivery device for providing aromatherapy and/or for delivering medication to the user as the mask is heated. For example, in one embodiment, the fragrance or vapor delivery device may include a vapor or fragrance composition that emits an aroma and/or vapor when heated by the mask. The fragrance or vapor delivery device can be integral with the mask and incorporated into, for instance, an outer cover layer or the facing layer.

Alternatively, the vapor or fragrance delivery device can be a separate component that is attached to or removed from the mask as desired. For instance, in one embodiment, the vapor or fragrance delivery device can be supplied to consumers attached to the mask. If desired, a user may then remove the delivery device if the user prefers to have heat only. In still another embodiment, the vapor or fragrance delivery device can be contained in a separate sealed package. The separate sealed package can be contained within the sealed package containing the mask or may be contained in a kit that includes a first sealed package for the mask and a second sealed package for the vapor or fragrance delivery device. The kit may include only a single vapor or fragrance delivery device or may include multiple devices. When containing multiple devices, a user can decide how many of the vapor or fragrance delivery devices to attach to the mask and may also determine the location of where the vapor or fragrance delivery devices are positioned.

Figure 4:
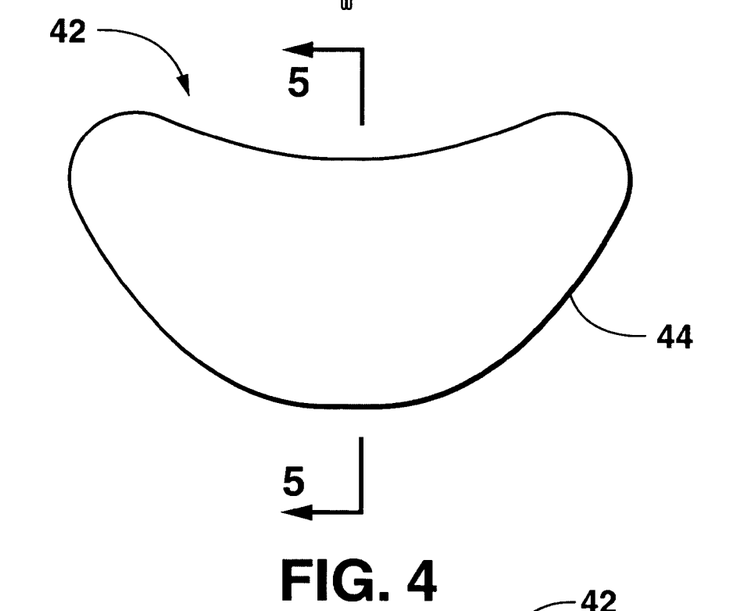
FIG. 4 is a perspective view of one embodiment of a vapor or fragrance delivery device that may be used in conjunction with a warming mask in accordance with the present disclosure.
Figure 5:
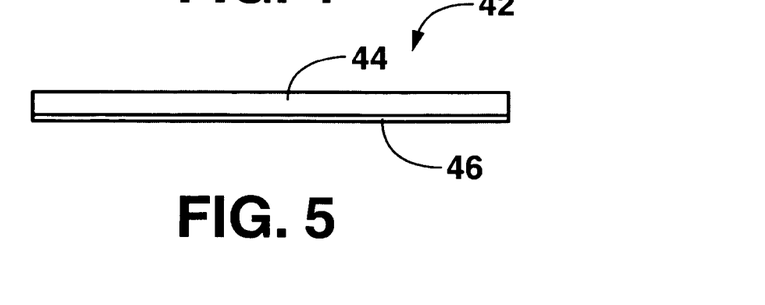
FIG. 5 is a cross-sectional view of the vapor or fragrance delivery device illustrated in FIG. 4.

One embodiment of a fragrance or vapor delivery device, for instance, is illustrated in FIGS. 4 and 5. The shape of the fragrance or vapor delivery device can vary depending upon various factors including the shape of the mask and the location where the delivery devices are to be positioned. In the embodiment illustrated in FIG. 4, for instance, the fragrance or vapor delivery device has a shape configured to surround the nose of a user, such as below the eye openings of the mask on the cheek portions 22 and 24. In other embodiments, however, the fragrance or vapor delivery devices may have a rectangular shape, a circular shape, an ovular shape, a square shape, a triangular shape, or any other suitable curved or complex shape. For instance, in an alternative embodiment, the fragrance or vapor delivery devices may have a shape that generally conforms to the shape of the thermal delivery pads.

As shown, a fragrance or vapor delivery device 42 can include a substrate 44 containing a vapor or fragrance composition. The fragrance or vapor delivery device 42 can also include any suitable attachment device capable of attaching the fragrance or vapor delivery device to the mask 14. For instance, as shown in FIG. 5, the fragrance or vapor delivery device 42 can include an adhesive layer 46. In general, any suitable adhesive may be used to form the adhesive layer 46. In one embodiment, for instance, a pressure sensitive adhesive may be used.

When packaged with the mask 14, the adhesive layer 46 can be covered with a release layer, such as a paper layer or film layer coated with a silicone. The release layer is removed exposing the adhesive layer 46. A user can then attach the fragrance or vapor delivery device 42 to the mask 14 using the adhesive layer 46 at any suitable location. The fragrance or vapor delivery device 42 can also be removed from the mask as desired. For instance, in one embodiment, the fragrance or vapor delivery device 42 may be attached to the mask 14 initially and then removed during heat treatment.

Figure 7:
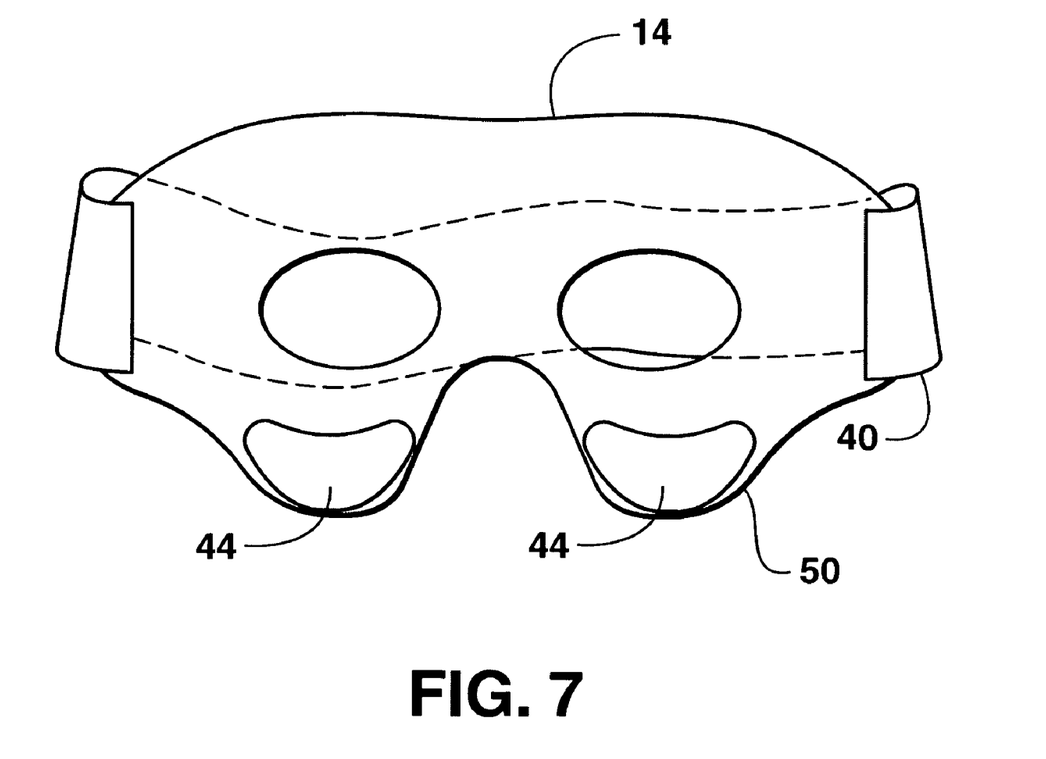
FIG. 7 is a perspective view of a warming mask in accordance with the present disclosure illustrating attachment of vapor or fragrance delivery devices.

As described above, the mask 14 can be packaged with a single fragrance or vapor delivery device 42 or with multiple fragrance or vapor delivery devices. For instance, as shown in FIG. 7, a mask 14 is illustrated containing a first fragrance or vapor delivery device 42 and a second fragrance or vapor delivery device 50. In this embodiment, the fragrance or vapor delivery devices 42 and 50 are attached to the cheek portions 22 and 24 of the mask 14. In this manner, the fragrance or vapor delivery devices surround the nose of a user as the mask is heated. Thus, as the fragrance or vapor delivery devices emit a vapor, a fragrance, or both. The function of the fragrance or vapor delivery device can vary depending upon the particular application. For instance, in one embodiment, the fragrance or vapor delivery device may be used simply to emit a pleasant smell for the user. In an alternative embodiment, the fragrance or vapor delivery device may emit a medicant intended to be inhaled by the user for providing, for instance, sinus relief.

It should be understood, however, that the mask 14 can include fewer or greater numbers of fragrance or vapor delivery devices than the two illustrated in FIG. 7.

The fragrance or vapor composition present in the fragrance or vapor delivery device can vary depending upon the particular application and the desired result. For instance, the composition present in the delivery device can vary whether or not the mask is used to treat an ailment, such as a sinus problem, or whether the mask is to be used simply for therapeutic purposes, such as in a spa setting.

In one embodiment, for instance, the fragrance or vapor composition can contain one or more essential oils. Essential oils are highly odoriferous, liquid components obtained from plant tissue (e.g., flowers, bark, leaves, seeds, roots, etc.), often captured by steam distillation or other processes and typically including a mixture of one or more terpenes, esters, aldehydes, ketones, alcohols, phenols, and/or oxides, for example. Essential oils can be included in the mask for providing a pleasant scent. Alternatively, the essential oils may be used to help calm the user while the mask is in place. In this regard, the essential oils may be positioned on the mask around the nose of a user for inhaling a scent. Alternatively, the essential oils may be positioned along the temple and forehead of a user for other therapeutic purposes.

Commonly used essential oils include those derived from angelica root, anise, balsam (Peru or other balsams), basil, bay laurel, beeswax, benzoin, bergamot, bois-de-rose, boronia, cajeput, cardamom, carrot seed, cedarwood (Atlas or Virginian), chamomile (German or Roman), cinnamon, citronella, clary sage, clove bud, coriander, cypress, dill, elemi, eucalyptus, fennel, fir needle, frankincense, galbanum, geranium, ginger, grapefruit, helichrysum, hyssop, immortelle, jasmine, juniper berry, kanuka, lavender, lavendin, lemon, lemongrass, lime, linden blossom, mandarin, manuka, marjoram, may chang, myrrh, myrtle, neroli, niaouli, nutmeg, oakmoss, olibanum, orange (bitter or sweet), oregano, palmarosa, parsley, patchouli, pepper, black, peppermint, petitgrain, pine (Scotch, white, or Siberian), ravensara, rose, rosemary, rosewood, sandalwood, spearmint, spikenard, spruce, tagetes, tangerine, tea tree (common, lemon, or New Zealand), thyme, tobacco, tuberose, vanilla, vetiver, violet leaf, yarrow, ylang ylang, and so forth. Further information on essential oils and other herbal extracts that can be considered for use in the present invention are discussed in U.S. Pat. No. 6,280,751, issued Aug. 28, 2001 to Fletcher and Hargreaves and in US 20040071757, published Apr. 15, 2004 by D. Rolf, both of which are herein incorporated by reference.

In addition to essential oils, the composition used in the present disclosure can also include other natural products or extracts such as absolutes, resinoids, resins etc., and synthetic compositions as well as mixtures of synthetic and natural fragrances. Synthetic fragrance components may include, by way of example, hydrocarbons, alcohols, aldehydes, ketones ethers, acids, esters, acetals, ketals, nitrites, phenols, etc. including saturated and unsaturated compounds, aliphatic, alicyclic, heterocyclic and aromatic compounds. Examples of such perfume components are given by D. H. Pybus and C. S. Sell in *The Chemistry of Fragrances* (Springer Verlag, 1999).

When the mask 14 is used to treat respiratory conditions, such as congestion, sinus pressure, and the like, the fragrance or vapor composition can contain an aromatic decongestant. Aromatic decongestants that may be used include oil of wintergreen, menthol, thymol, camphor, oil of peppermint, eucalyptus oil, phenylephrine hydrochloride, pheniramine maleate, benzalkonium chloride, methyl salicylate, pseudoephedrine hydrochloride, oxymetazoline hydrochloride, xylometazoline hydrochloride, methazoline hydrochloride, epinephrine, spirits of turpentine, ephedra (ma huang), coltsfoot (Tussilago farfara L.), ginger (Zingiber officinale), napazoline hydrochloride, and other decongestants known in the art. Other aromatic compounds that may be used in the composition include 3-1-menthoxy propane-1,2-dial, N-substituded-p-menthane-3-carboxamides, acyclic carboxamides, and mixtures thereof.

The above aromatic compounds can be present alone or in combination with various other ingredients to form the composition that is applied to the fragrance or vapor delivery device. For instance, stabilizers and thickeners may also be contained in the composition. In addition, solvents and viscosity modifiers may also be used in order to facilitate application to the substrate 44.

In one embodiment, the fragrance or vapor composition is in a form that does not release substantial amounts of the aromatic components until the composition is heated. For instance, in one embodiment, the fragrance or vapor composition may be microencapsulated. The microcapsules may be made from a material that ruptures after a particular temperature is reached.

The fragrance or vapor composition can be applied to the substrate 44 of the fragrance or vapor delivery device 42 using any suitable technique. For instance, the composition can be sprayed, printed, or coated onto the substrate. The substrate 44 can comprise any suitable material capable of retaining the fragrance or vapor composition. For instance, the substrate 44 can be made from any suitable textile material such as a nonwoven material, a woven material, a knitted material, or a paper.

Figure 6:
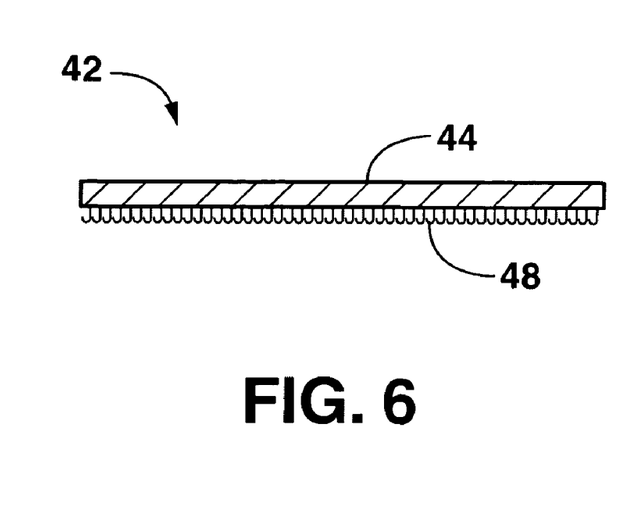
FIG. 6 is a side view of an alternative embodiment of a vapor or fragrance delivery device made in accordance with the present disclosure.

In the embodiment illustrated in FIG. 5, the fragrance or vapor delivery device 42 includes an adhesive layer 46. Referring to FIG. 6, an alternative embodiment of a fragrance or vapor delivery device 42 is illustrated. In the embodiment illustrated in FIG. 6, the attachment device comprises a plurality of hook attachments 48. The hook attachments 48 are for attaching the fragrance or vapor delivery device to the mask 14. The hooks 48, for instance, may form a hook and loop attachment to the mask. In this regard, the exterior surface of the mask can include a suitable loop material. For instance, in one embodiment, the mask can include an outer cover layer made from a nonwoven material.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged either in whole or in part. Furthermore, those of ordinary skill in the art will appreciate that the foregoing description is by way of example only, and is not intended to limit the invention so further described in such appended claims.

What is claimed:

1. A warming mask product comprising:
a sealed package;
a mask having a shape configured to cover at least a portion of a person's face defining a first eye opening spaced from a second eye opening, the mask comprising at least one thermal delivery pad, the thermal delivery pad comprising an exothermic composition contained in a sealed compartment, the compartment comprising a gas permeable polymer film, the sealed compartment having a first side configured to face a user and a second and opposite side, the gas permeable polymer film being present only at the second side, the mask further comprising a facing layer located on the first side of the sealed compartment, the facing layer defining an exterior surface configured to contact a user's face, the exterior surface comprising a textile material; and
wherein, once the sealed package is opened air passes through the gas permeable polymer film and reacts with the exothermic composition thereby releasing heat.

2. A warming mask product as defined in claim 1, wherein the sealed compartment reaches an elevated temperature when removed from the sealed package, the elevated temperature being at least 38° C.

3. A warming mask product as defined in claim 2, wherein the elevated temperature is from about 40° C. to about 45° C.

4. A warming mask as defined in claim 1, wherein the exothermic composition comprises an oxidizable metal.

5. A warming mask as defined in claim 4, wherein the oxidizable metal comprises iron, an alloy thereof, or an oxide thereof.

6. A warming mask product as defined in claim 4, wherein the oxidizable metal comprises zinc, aluminum, magnesium, alloys thereof, or mixtures thereof.

7. A warming mask product as defined in claim 4, wherein the exothermic composition further comprises water.

8. A warming mask product as defined in claim 2, wherein, when removed from the sealed package, the thermal delivery pad is configured to stay at the elevated temperature for at least about 15 minutes.

9. A warming mask product as defined in claim 2, wherein, when removed from the sealed package, the thermal delivery pad is configured to stay at the elevated temperature for at least about one hour.

10. A warming mask product as defined in claim 1, the mask further including a forehead portion positioned over the eye openings and cheek portions that extend down from the eye openings and are configured to border the nose of a wearer.

11. A warming mask product as defined in claim 10, wherein the mask product includes a first thermal delivery pad and a second thermal delivery pad, the first thermal delivery pad partially encircling the first eye opening and the second thermal delivery pad partially encircling the second eye opening.

12. A warming mask product as defined in claim 10, wherein the mask product includes a single thermal delivery pad, the thermal delivery pad extending over the eye openings and into the cheek portions.

13. A warming mask product as defined in claim 1, further comprising a strap configured to secure the mask to a head of a user.

14. A warming mask product as defined in claim 1, further comprising a body adhesive present on the facing layer for securing the mask to a face of a user.

15. A warming mask product as defined in claim 14, wherein the body adhesive comprises a hydrogel.

16. A warming mask product as defined in claim 1, further comprising an outer cover layer, the at least one thermal delivery pad being positioned in between the outer cover layer and the facing layer.

17. A warming mask product as defined in claim 1, further comprising a vapor or fragrance delivery device that includes an attachment device for attaching the vapor or fragrance delivery device to the mask.

18. A warming mask product as defined in claim 17, wherein the vapor or fragrance delivery device is configured to be attached to the mask after the mask is removed from the sealed package.

19. A warming mask product as defined in claim 17, wherein the attachment device comprises mechanical hooks or an adhesive.

20. A warming mask product as defined in claim 17, wherein the vapor or fragrance delivery device comprises a substrate containing a vapor or fragrance composition, the vapor or fragrance composition releasing a vapor, a fragrance, or both as the thermal delivery pad is heated.

21. A warming mask product as defined in claim 1, wherein the mask includes a first exterior surface configured to contact a user's face and a second and opposite exterior surface, the second and opposite exterior surface including at least one design element configured to improve the aesthetic appeal of the mask.

22. A warming mask product as defined in claim 1, wherein the mask includes a first exterior surface configured to contact a user's face and a second and opposite exterior surface, the second exterior surface including an indicia for indicating that the user is sick.

23. A warming mask product as defined in claim 22, wherein the indicia comprises a color, a pattern, a design, or a logo.

24. A warming mask product as defined in claim 17, wherein the vapor or fragrance delivery device is removable from the mask.

25. A warming mask product as defined in claim 1, wherein at least one gas impermeable strip is removably affixed to the gas permeable polymer film.

26. A warming mask product comprising:
a sealed package containing a mask, the mask having a shape configured to cover at least a portion of a person's face, the mask comprising at least one thermal delivery pad, the thermal delivery pad comprising an exothermic composition contained in a sealed compartment, the compartment comprising a gas permeable polymer film, the thermal delivery pad having a first side configured to face a user and a second and opposite side the mask further comprising a facing layer located on the first side of the thermal delivery pad, the facing layer defining an exterior surface configured to contact a user's face including a first eye opening spaced from a second eye opening;
a vapor or fragrance delivery device that includes an attachment device for attaching the vapor or fragrance delivery device to the mask, the vapor or fragrance delivery device being configured to be attached to the mask after the mask has been removed from the sealed package; and
wherein, once the sealed package is opened and the vapor and fragrance delivery device is attached to the mask, air passes through the gas permeable polymer film and reacts with the exothermic composition thereby releasing heat.

27. A warming mask product as defined in claim 26, wherein the sealed compartment reaches an elevated temperature when removed from the sealed package, the elevated temperature being at least 38° C.

28. A warming mask product as defined in claim 26, the mask further including a forehead portion positioned over the eye openings and cheek portions that extend down from the eye openings and are configured to border the nose of a wearer, the vapor or fragrance delivery device being configured to attach to at least one of the cheek portions.

29. A warming mask product as defined in claim 26, wherein the attachment device comprises mechanical hooks or an adhesive.

30. A warming mask product as defined in claim 26, wherein the vapor or fragrance delivery device comprises a substrate containing a vapor or fragrance composition, the vapor or fragrance composition releasing a vapor, a fragrance, or both as the thermal delivery pad is heated.

31. A warming mask product as defined in claim 28, further comprising an outer cover layer, the at least one thermal delivery pad being positioned in between the outer cover layer and the facing layer.

32. A warming mask product as defined in claim 26, wherein the thermal delivery pad reaches an elevated temperature when removed from the sealed package, the elevated temperature being from about 40° to about 45° C.

33. A warming mask product as defined in claim 28, wherein the mask defines an open portion below the nose of a wearer that provides access to a wearer's nostrils.

34. A warming mask product as defined in claim 26, wherein the mask is contained in a first sealed package and the vapor or fragrance delivery device is contained in a second sealed package.

35. A warming mask product as defined in claim 26, wherein at least one gas impermeable strip is removably affixed to the gas permeable polymer film.

\* \* \* \* \*